(12) United States Patent
Your (10) Patent No.: US 8,158,712 B2
(45) Date of Patent: Apr. 17, 2012

(54) POLYMERIC MATERIALS SUITABLE FOR OPHTHALMIC DEVICES AND METHODS OF MANUFACTURE

(75) Inventor: Jingjong Your, Cupertino, CA (US)

(73) Assignee: PowerVision, Inc., Belmont, CA (US)

( * ) Notice: Subject to any disclaimer, the term of this patent is extended or adjusted under 35 U.S.C. 154(b) by 321 days.

(21) Appl. No.: 12/034,942

(22) Filed: Feb. 21, 2008

(65) Prior Publication Data

US 2008/0200982 A1  Aug. 21, 2008

Related U.S. Application Data

(60) Provisional application No. 60/902,593, filed on Feb. 21, 2007.

(51) Int. Cl.
- C08L 31/00 (2006.01)
- G02B 1/04 (2006.01)
- A61F 2/14 (2006.01)
- A61F 2/16 (2006.01)
- C08F 118/02 (2006.01)

(52) U.S. Cl. ........ 524/556; 523/106; 623/4.1; 623/6.11; 623/6.37; 526/319

(58) Field of Classification Search .................. 524/556; 523/106; 623/4.1, 6.11, 6.37; 526/319
See application file for complete search history.

(56) References Cited

U.S. PATENT DOCUMENTS

| | | |
|---|---|---|
| 4,111,995 A | 9/1978 | Nelson |
| 4,253,199 A | 3/1981 | Banko |
| 4,254,509 A | 3/1981 | Tennant |
| 4,304,895 A | 12/1981 | Loshaek |
| 4,373,218 A | 2/1983 | Schachar |
| 4,409,691 A | 10/1983 | Levy |
| 4,423,809 A | 1/1984 | Mazzocco |
| 4,435,856 A | 3/1984 | L'Esperance |
| 4,466,705 A | 8/1984 | Michelson |
| 4,490,860 A | 1/1985 | Rainin |
| 4,494,254 A | 1/1985 | Lopez |
| 4,512,040 A | 4/1985 | McClure |
| 4,528,311 A | 7/1985 | Beard et al. |
| 4,575,373 A | 3/1986 | Johnson |
| 4,585,457 A | 4/1986 | Kalb |
| 4,604,295 A | 8/1986 | Humphreys |
| 4,615,701 A | 10/1986 | Woods |
| 4,620,954 A | 11/1986 | Singer et al. |
| 4,685,921 A | 8/1987 | Peyman |
| 4,685,922 A | 8/1987 | Peyman |
| 4,693,717 A | 9/1987 | Michelson |
| 4,720,286 A | 1/1988 | Bailey et al. |
| 4,731,078 A | 3/1988 | Stoy et al. |
| 4,731,079 A | 3/1988 | Stoy |
| 4,731,080 A | 3/1988 | Galin |
| 4,784,485 A | 11/1988 | Ho |
| 4,787,903 A | 11/1988 | Grendahl |
| 4,790,847 A | 12/1988 | Woods |
| 4,813,956 A | 3/1989 | Gupta |
| 4,816,031 A | 3/1989 | Pfoff |
| 4,834,750 A | 5/1989 | Gupta |
| 4,836,201 A | 6/1989 | Patton et al. |
| 4,842,601 A | 6/1989 | Smith |
| 4,848,343 A | 7/1989 | Wallsten et al. |
| 4,888,012 A | 12/1989 | Horn et al. |
| 4,892,543 A | 1/1990 | Turely |
| 4,902,293 A | 2/1990 | Feaster |
| 4,919,151 A | 4/1990 | Grubbs et al. |
| 4,932,966 A | 6/1990 | Christie et al. |
| 4,946,469 A | 8/1990 | Sarfarazi |
| 4,950,289 A | 8/1990 | Krasner |
| 4,963,148 A | 10/1990 | Sulc et al. |
| 4,994,082 A | 2/1991 | Richards et al. |
| 4,995,879 A | 2/1991 | Dougherty |
| 4,995,880 A | 2/1991 | Galib |
| 5,015,254 A | 5/1991 | Greite |
| 5,035,710 A | 7/1991 | Nakada et al. |
| 5,047,051 A | 9/1991 | Cumming |
| 5,061,914 A | 10/1991 | Busch et al. |
| 5,066,301 A | 11/1991 | Wiley |
| 5,145,884 A | 9/1992 | Yamamoto et al. |
| 5,145,935 A | 9/1992 | Hayashi |
| 5,152,789 A | 10/1992 | Willis |
| 5,171,266 A | 12/1992 | Wiley et al. |
| 5,201,763 A | 4/1993 | Brady et al. |
| 5,213,579 A | 5/1993 | Yamada et al. |
| 5,224,957 A | 7/1993 | Gasser et al. |
| 5,235,003 A | 8/1993 | Ward et al. |
| 5,251,993 A | 10/1993 | Sigourney |
| 5,275,623 A | 1/1994 | Sarfarazi |

(Continued)

FOREIGN PATENT DOCUMENTS

EP    0898972 A2    3/1999

(Continued)

OTHER PUBLICATIONS

Your, Jingjong; U.S. Appl. No. 12/177,720 entitled "Lens material and methods of curing with UV light," filed Jul. 22, 2008.

(Continued)

*Primary Examiner* — Michael M Bernshteyn
(74) *Attorney, Agent, or Firm* — Shay Glenn LLP (57) ABSTRACT

Biocompatible polymers useful in ophthalmic devices such as accommodating intraocular lenses. The polymers have improved resistance to the diffusion of fluid, relatively high refractive indexes, and mechanical properties to allow for deformation upon the application of force.

14 Claims, 2 Drawing Sheets

U.S. PATENT DOCUMENTS

| | | |
|---|---|---|
| 5,275,624 A | 1/1994 | Hara et al. |
| 5,288,293 A | 2/1994 | O'Donnell, Jr. |
| 5,290,892 A | 3/1994 | Namdaran et al. |
| 5,326,347 A | 7/1994 | Cumming |
| 5,405,386 A | 4/1995 | Rheinish et al. |
| 5,443,506 A | 8/1995 | Garabet |
| 5,444,106 A | 8/1995 | Zhou et al. |
| 5,476,514 A | 12/1995 | Cumming |
| 5,489,302 A | 2/1996 | Skottun |
| 5,496,366 A | 3/1996 | Cumming |
| 5,506,300 A | 4/1996 | Ward et al. |
| 5,512,609 A | 4/1996 | Yang |
| 5,578,081 A | 11/1996 | McDonald |
| 5,585,049 A | 12/1996 | Grisoni et al. |
| 5,593,436 A | 1/1997 | Langerman |
| 5,607,472 A | 3/1997 | Thompson |
| 5,628,795 A | 5/1997 | Langerman |
| 5,665,822 A | 9/1997 | Bitler et al. |
| 5,674,282 A | 10/1997 | Cumming |
| 5,697,973 A | 12/1997 | Peyman et al. |
| 5,702,441 A | 12/1997 | Zhou |
| 5,774,273 A | 6/1998 | Bornhorst |
| 5,776,191 A | 7/1998 | Mazzocco |
| 5,776,192 A | 7/1998 | McDonald |
| 5,814,680 A | 9/1998 | Imafuku et al. |
| 5,843,188 A | 12/1998 | McDonald |
| 5,891,931 A | 4/1999 | Leboeuf et al. |
| 5,922,821 A | 7/1999 | LeBoeuf et al. |
| 5,928,282 A | 7/1999 | Nigam |
| 5,964,802 A | 10/1999 | Anello et al. |
| 5,984,962 A | 11/1999 | Anello et al. |
| 6,013,101 A | 1/2000 | Israel |
| 6,015,842 A | 1/2000 | Leboeuf et al. |
| 6,102,539 A | 8/2000 | Tucker |
| 6,117,171 A | 9/2000 | Skottun |
| 6,124,980 A | 9/2000 | Cerbell |
| 6,139,576 A | 10/2000 | Doyle et al. |
| 6,140,438 A | 10/2000 | Ojio et al. |
| 6,160,084 A | 12/2000 | Langer et al. |
| 6,176,878 B1 | 1/2001 | Gwon et al. |
| 6,180,687 B1 | 1/2001 | Hammer et al. |
| 6,188,526 B1 | 2/2001 | Sasaya et al. |
| 6,190,410 B1 | 2/2001 | Lamielle et al. |
| 6,195,807 B1 | 3/2001 | Chou |
| 6,197,059 B1 | 3/2001 | Cumming |
| 6,217,612 B1 | 4/2001 | Woods |
| 6,225,367 B1 | 5/2001 | Chaouk et al. |
| 6,245,106 B1 | 6/2001 | Makker et al. |
| 6,299,641 B1 | 10/2001 | Woods |
| 6,302,911 B1 | 10/2001 | Hanna |
| 6,322,589 B1 | 11/2001 | Cumming |
| 6,342,073 B1 | 1/2002 | Cumming et al. |
| 6,387,126 B1 | 5/2002 | Cumming |
| 6,388,043 B1 | 5/2002 | Langer et al. |
| 6,406,494 B1 | 6/2002 | Laguette et al. |
| 6,413,262 B2 | 7/2002 | Saishin et al. |
| 6,423,094 B1 | 7/2002 | Sarfarazi |
| 6,443,985 B1 | 9/2002 | Woods |
| 6,450,642 B1 | 9/2002 | Jethmalani et al. |
| 6,464,725 B2 | 10/2002 | Skottun |
| 6,488,708 B2 | 12/2002 | Sarfarazi |
| 6,493,151 B2 | 12/2002 | Schachar |
| 6,503,276 B2 | 1/2003 | Lang et al. |
| 6,517,577 B1 | 2/2003 | Callahan et al. |
| 6,551,354 B1 | 4/2003 | Ghazizadeh et al. |
| 6,552,860 B1 | 4/2003 | Alden |
| 6,554,859 B1 | 4/2003 | Lang et al. |
| 6,555,030 B1 | 4/2003 | Weinschenk, III |
| 6,585,768 B2 | 7/2003 | Hamano et al. |
| 6,589,550 B1 | 7/2003 | Hodd et al. |
| 6,592,621 B1 | 7/2003 | Domino |
| 6,599,317 B1 | 7/2003 | Weinschenk, III et al. |
| 6,601,956 B1 | 8/2003 | Jean et al. |
| 6,610,350 B2 | 8/2003 | Suzuki et al. |
| 6,616,691 B1 | 9/2003 | Tran |
| 6,616,692 B1 | 9/2003 | Glick et al. |
| 6,638,304 B2 | 10/2003 | Azar |
| 6,638,305 B2 | 10/2003 | Laguette |
| 6,638,306 B2 | 10/2003 | Cumming |
| 6,645,245 B1 | 11/2003 | Preussner |
| 6,645,246 B1 | 11/2003 | Weinschenk, III et al. |
| 6,656,223 B2 | 12/2003 | Brady |
| 6,660,035 B1 | 12/2003 | Lang et al. |
| 6,692,525 B2 | 2/2004 | Brady et al. |
| 6,695,881 B2 | 2/2004 | Peng et al. |
| 6,709,108 B2 | 3/2004 | Levine et al. |
| 6,712,848 B1 | 3/2004 | Wolf et al. |
| 6,713,583 B2 | 3/2004 | Liao et al. |
| 6,730,123 B1 | 5/2004 | Klopotek |
| 6,743,388 B2 | 6/2004 | Sridharan et al. |
| 6,749,632 B2 | 6/2004 | Sandstedt et al. |
| 6,749,634 B2 | 6/2004 | Hanna |
| 6,786,934 B2 | 9/2004 | Zadno-Azizi et al. |
| 6,818,158 B2 | 11/2004 | Pham et al. |
| 6,827,738 B2 | 12/2004 | Willis et al. |
| 6,836,374 B2 | 12/2004 | Esch et al. |
| 6,852,793 B2 | 2/2005 | Salamone et al. |
| 6,860,601 B2 | 3/2005 | Shadduck |
| 6,878,320 B1 | 4/2005 | Alderson et al. |
| 6,884,261 B2 | 4/2005 | Zadno-Azizi et al. |
| 6,899,732 B2 | 5/2005 | Zadno-Azizi et al. |
| 6,899,850 B2 | 5/2005 | Haywood et al. |
| 6,926,736 B2 | 8/2005 | Peng et al. |
| 6,935,743 B2 | 8/2005 | Shadduck |
| 6,966,649 B2 | 11/2005 | Shadduck |
| 6,969,403 B2 | 11/2005 | Peng et al. |
| 7,060,094 B2 | 6/2006 | Shahinpoor et al. |
| 7,068,439 B2 | 6/2006 | Esch et al. |
| 7,104,648 B2 | 9/2006 | Dahi et al. |
| 7,122,053 B2 | 10/2006 | Esch |
| 7,144,423 B2 | 12/2006 | McDonald |
| 7,217,288 B2 | 5/2007 | Esch et al. |
| 7,241,312 B2 | 7/2007 | Lai et al. |
| 7,247,689 B2 | 7/2007 | Makker et al. |
| 7,264,351 B2 | 9/2007 | Shadduck |
| 7,278,739 B2 | 10/2007 | Shadduck |
| 7,322,694 B2 | 1/2008 | Dahi et al. |
| 7,416,300 B2 | 8/2008 | Wei et al. |
| 7,494,505 B2 | 2/2009 | Kappelhof et al. |
| 7,753,953 B1 | 7/2010 | Yee |
| 2001/0001836 A1 | 5/2001 | Cumming |
| 2001/0016771 A1 | 8/2001 | Cumming |
| 2001/0039449 A1 | 11/2001 | Johnson et al. |
| 2002/0046783 A1 | 4/2002 | Johnson et al. |
| 2002/0055777 A1 | 5/2002 | Cumming et al. |
| 2002/0072795 A1 | 6/2002 | Green |
| 2002/0095212 A1 | 7/2002 | Boehm |
| 2002/0107568 A1 | 8/2002 | Zadno-Azizi et al. |
| 2002/0111678 A1 | 8/2002 | Zadno-Azizi et al. |
| 2002/0116057 A1 | 8/2002 | Ting et al. |
| 2002/0116058 A1 | 8/2002 | Zadno-Azizi et al. |
| 2002/0116059 A1 | 8/2002 | Zadno-Azizi et al. |
| 2002/0116060 A1 | 8/2002 | Nguyen et al. |
| 2002/0116061 A1 | 8/2002 | Zadno-Azizi et al. |
| 2002/0133228 A1 | 9/2002 | Sarver |
| 2002/0161434 A1 | 10/2002 | Laguette et al. |
| 2002/0161435 A1 | 10/2002 | Portney |
| 2002/0177896 A1 | 11/2002 | Israel |
| 2002/0193876 A1 | 12/2002 | Lang et al. |
| 2003/0003295 A1 | 1/2003 | Dreher et al. |
| 2003/0004569 A1 | 1/2003 | Haefliger |
| 2003/0018384 A1 | 1/2003 | Valyunin et al. |
| 2003/0042176 A1 | 3/2003 | Alderson et al. |
| 2003/0050695 A1 | 3/2003 | Lin et al. |
| 2003/0050696 A1 | 3/2003 | Cumming |
| 2003/0060878 A1 | 3/2003 | Shadduck |
| 2003/0060881 A1 | 3/2003 | Glick et al. |
| 2003/0078656 A1 | 4/2003 | Nguyen |
| 2003/0078657 A1 | 4/2003 | Zadno-Azizi et al. |
| 2003/0078658 A1 | 4/2003 | Zadno-Azizi et al. |
| 2003/0083744 A1 | 5/2003 | Khoury |
| 2003/0109925 A1 | 6/2003 | Ghazizadeh et al. |
| 2003/0109926 A1 | 6/2003 | Portney |
| 2003/0130732 A1 | 7/2003 | Sarfarazi |
| 2003/0135272 A1 | 7/2003 | Brady et al. |
| 2003/0149480 A1 | 8/2003 | Shadduck |
| 2003/0158599 A1 | 8/2003 | Brady et al. |

| | | | |
|---|---|---|---|
| 2003/0171808 A1 | 9/2003 | Phillips | |
| 2003/0183960 A1 | 10/2003 | Buazza et al. | |
| 2003/0187505 A1 | 10/2003 | Liao | |
| 2003/0199977 A1 | 10/2003 | Cumming | |
| 2004/0001180 A1 | 1/2004 | Epstein | |
| 2004/0006386 A1 | 1/2004 | Valint et al. | |
| 2004/0006387 A1 | 1/2004 | Kelman | |
| 2004/0008419 A1 | 1/2004 | Schachar | |
| 2004/0015236 A1 | 1/2004 | Sarfarazi | |
| 2004/0039446 A1 | 2/2004 | McNicholas | |
| 2004/0054408 A1 | 3/2004 | Glick et al. | |
| 2004/0059343 A1 | 3/2004 | Shearer et al. | |
| 2004/0082993 A1 | 4/2004 | Woods | |
| 2004/0082994 A1 | 4/2004 | Woods et al. | |
| 2004/0085511 A1 | 5/2004 | Uno et al. | |
| 2004/0111151 A1 | 6/2004 | Paul et al. | |
| 2004/0111152 A1 | 6/2004 | Kelman | |
| 2004/0111153 A1 | 6/2004 | Woods et al. | |
| 2004/0127984 A1 | 7/2004 | Paul et al. | |
| 2004/0162612 A1 | 8/2004 | Portney et al. | |
| 2004/0181279 A1 | 9/2004 | Nun | |
| 2004/0190153 A1 | 9/2004 | Esch | |
| 2004/0230203 A1 | 11/2004 | Yaguchi | |
| 2005/0021139 A1 | 1/2005 | Shadduck | |
| 2005/0119740 A1 | 6/2005 | Esch et al. | |
| 2005/0131535 A1 | 6/2005 | Woods | |
| 2005/0149183 A1 | 7/2005 | Shadduck | |
| 2005/0165410 A1 | 7/2005 | Zadno-Azizi et al. | |
| 2005/0251253 A1 | 11/2005 | Gross | |
| 2005/0264756 A1 | 12/2005 | Esch | |
| 2006/0041307 A1 | 2/2006 | Esch et al. | |
| 2006/0069433 A1 | 3/2006 | Ben Nun | |
| 2006/0100703 A1 | 5/2006 | Evans et al. | |
| 2006/0184181 A1 | 8/2006 | Cole et al. | |
| 2006/0253196 A1 | 11/2006 | Woods | |
| 2007/0005136 A1 | 1/2007 | Richardson | |
| 2007/0010880 A1 | 1/2007 | Esch | |
| 2007/0021831 A1 | 1/2007 | Clarke | |
| 2007/0050023 A1 | 3/2007 | Bessiere et al. | |
| 2007/0078515 A1 | 4/2007 | Brady | |
| 2007/0088433 A1 | 4/2007 | Esch et al. | |
| 2007/0100445 A1 | 5/2007 | Shadduck | |
| 2007/0106377 A1 | 5/2007 | Smith et al. | |
| 2007/0129801 A1 | 6/2007 | Cumming | |
| 2007/0162112 A1 | 7/2007 | Burriesci et al. | |
| 2007/0203578 A1 | 8/2007 | Scholl et al. | |
| 2007/0213817 A1 | 9/2007 | Esch et al. | |
| 2007/0244561 A1 | 10/2007 | Ben Nun | |
| 2007/0299487 A1 | 12/2007 | Shadduck | |
| 2008/0004699 A1 | 1/2008 | Ben Nun | |
| 2008/0015689 A1 | 1/2008 | Esch et al. | |
| 2008/0027537 A1 | 1/2008 | Gerlach et al. | |
| 2008/0139769 A1* | 6/2008 | Iwamoto et al. | 526/259 |
| 2008/0188930 A1 | 8/2008 | Mentak et al. | |
| 2008/0269887 A1 | 10/2008 | Cumming | |
| 2008/0269987 A1 | 10/2008 | Barron et al. | |
| 2008/0300680 A1 | 12/2008 | Ben Nun | |
| 2009/0228101 A1 | 9/2009 | Zadno-Azizi | |
| 2009/0234449 A1 | 9/2009 | DeJuan, Jr. et al. | |
| 2009/0264998 A1 | 10/2009 | Mentak et al. | |
| 2009/0312836 A1 | 12/2009 | Pinchuk et al. | |
| 2010/0063588 A1 | 3/2010 | Park | |
| 2010/0228344 A1 | 9/2010 | Shadduck | |
| 2010/0228346 A1 | 9/2010 | Esch | |

FOREIGN PATENT DOCUMENTS

| | | |
|---|---|---|
| FR | 2784575 | 4/2000 |
| JP | 07-044938 | 5/1995 |
| JP | 9294754 | 11/1997 |
| JP | 10-206609 | 8/1998 |
| JP | 11276509 | 10/1999 |
| WO | WO 97/06751 A | 2/1997 |
| WO | WO 00/41650 A1 | 7/2000 |
| WO | WO 00/64655 A1 | 11/2000 |
| WO | WO 01/60286 A1 | 8/2001 |
| WO | WO 01/97742 A2 | 12/2001 |
| WO | WO 2004/010895 A2 | 2/2004 |
| WO | WO 2004/046768 A2 | 6/2004 |
| WO | WO 2004/072689 A2 | 8/2004 |
| WO | WO 2005/084588 A1 | 9/2005 |
| WO | WO 2006/004707 A2 | 1/2006 |
| WO | WO 2006/047383 A2 | 5/2006 |
| WO | WO 2006/088440 A1 | 8/2006 |
| WO | WO 2007/005529 A2 | 1/2007 |
| WO | WO 2007/030095 A1 | 3/2007 |
| WO | WO 2007/061688 A2 | 5/2007 |
| WO | WO 2009/100322 A2 | 8/2009 |

OTHER PUBLICATIONS

Smiley et al.; U.S. Appl. No. 12/177,857 entitled "Accommodating intraocular lenses and methods of use," filed Jul. 22, 2008.

Smiley et al.; U.S. Appl. No. 12/178,304 entitled "Post-implant accommodating lens modification," filed Jul. 23, 2008.

Smiley et al.; U.S. Appl. No. 12/17,565 entitled "Lens delivery system," filed Jul. 23, 2008.

Choi et al.; U.S. Appl. No. 12/178,454 entitled "Systems and methods for testing intraocular lenses," filed Jul. 23, 2008.

Baughman et al., "Negative poisson's ratios for extreme states fo matter," Science, vol. 288, pp. 1028-2022, Jun. 16, 2000.

Baughman, "Avoiding the shrink," Nature, vol. 425, pp. 667, Oct. 16, 2003.

Gordon, "Applications of shape memory polyurethanes," Proceedings of the First Intl Conf. on Shape Memory and Superelastic Tech., Asilomar Conference Center, Pacific Grove, CA, USA, pp. 115-119, 1994.

Jeon et al., "Shape memory and nonstructure in poly(norbornyl-POSS) copolymers," Polymer International, vol. 49, pp. 453-457, 2000.

Kim et al., "Polyurethanes having shape memory effects," Polymer, vol. 37, No. 26, pp. 5781-5793, 1996.

Lakes et al., "Dramatically stiffer elastic composite materials due to negative stiffness phase?," Journal of the Mechanics and Physics of Solids, vol. 50, pp. 979-1009, 2002.

Lakes et al., "Extreme damping in composite materials with negative-stiffness inclusions," Nature, vol. 410, pp. 565-567, Mar. 29, 2001.

Lakes, "A broader view of membranes," Nature, vol. 414, pp. 503-504, Nov. 29, 2001.

Lakes, "Extreme damping in compliant composites with a negative-stiffness phase," Philosophical Magazine Letters, vol. 81, No. 2, pp. 95-100, 2001.

Lakes, "Extreme damping in composite materials with a negative stiffness phase," Physical Review Letters, vol. 86, No. 13, pp. 2897-2899, Mar. 26, 2001.

Lakes, "Lateral deformations in extreme matter," Science, vol. 288, pp. 1976, Jun. 2000.

Lakes, "Negative poisson's ratio materials," Science, vol. 238, pp. 551, Oct. 23, 1987.

Lakes, "No contractile obligations," Nature, vol. 358, pp. 713-714, 1992.

Li et al., "Crystallinity and morphology of segmented polyurethanes with different soft-segment length," Journal of Applied Polymer Science, vol. 62, pp. 631-638, 1996.

Liu et al., "Thermomechanical characterization of a tailored series of shape memory polymers," Journal of Applied Medical Polymers, vol. 6, No. 2, 2002.

Mather et al., "Strain recovery in POSS hybrid thermoplastics," Polymer Preprints, vol. 41, No. 1, pp. 528-529, 2000.

Metcalfe et al., "Cold hibernated elastic memory foams for endovascular interventions," Biomaterials, vol. 24, pp. 491-497, 2003.

Lakes et al., "Microbuckling instability in elastomeric cellular sol-lids," J. Materials Science, vol. 28, pp. 4667-4672, 1993.

Takahashi et al., "Structure and properties of shape-memory polyurethane block copolymers," Journal of Applied Polymer Science, vol. 60, pp. 1061-1069, 1996.

Tobushi et al., "Thermomechanical properties of shape memory polymers of polyurethane series and their applications," Journal de Physique IV, Colloque C1, vol. 6, pp. 377-384, 1996.

Wang et al., "Deformation of extreme viscoelastic metals and composites," Materials Science and Enginerring A, vol. 370, pp. 41-49, 2004.

Wang et al., "Extreme stiffness systems due to negative stiffness elements," American Journal of Physics, vol. 72, No. 1, pp. 40-50, Jan. 2004.

Wang et al., "Stable extremely-high-damping discrete viscoelastic systems due to native stiffness elements," Applied Physics Letters, vol. 84, No. 22, pp. 4451-4453, May 31, 2004.

Xu et al., "Basic negative poisson's ratio microstructures by soft lithography," Advanced Materials, vol. 11, No. 14, 1999, pp. 1186-1189, 1999.

Smiley et al.; U.S. Appl. No. 12/178,565 entitled "Lens delivery system," filed Jul. 23, 2008.

Shadduck, John H.; U.S. Appl. No. 12/347,816 entitled "Intraocular lenses and business methods," filed Dec. 31, 2008.

Gruber et al.; Exhaustive soxhlet extraction for the complete removal of residual compounds . . . ; Journal of Biomedical Materials Research; vol. 53; No. 5; pp. 445-448; Mar. 2000.

Esch et al; U.S. Appl. No. 11/844,108 entitled "Accommodating Intraocular Lens System and Method" filed Aug. 23, 2007.

Smith et al; U.S. Appl. No. 11/844,087 entitled "Accommodating Intraocular Lens System Having Spherical Aberration Compensation and Method," filed Aug. 23, 2007.

Wyant et al; "Basic Wavefront Aberration Theory for Optical Metrology," Applied Optics and Optical Engineering, vol. XI, 1992:1-13.

Shadduck, John H.; U.S. Appl. No. 12/694,184 entitled "Intraocular Lenses and Business Methods," filed Jan. 26, 2010.

Argento et al.; U.S. Appl. No. 12/685,531 entitled "Intraocular Lenses and Methods of Accounting for Capsule Size Variability and Post-Implant Changes in the Eye," filed Jan. 11, 2010.

Lendlein et al., "Biodegradable, elastic shape-memory polymers for potential biomedical applications", Science; vol. 296; pp. 1673-1676; May 31, 2002.

Lendlein et al., "Shape-memory polymers," Angew. Chem. Int. Ed.; vol. 41; pp. 2034-2057; 2002.

Shadduck, John H.; U.S. Appl. No. 12/852,733 entitled "Intraocular Lens System and Method for Power Adjustment," filed Aug. 9, 2010.

Esch et al.; U.S. Appl. No. 12/853,892 entitled "Accommodating Intraocular Lens Having Peripherally Actuated Deflectable Surface and Method," filed Aug. 10, 2010.

Hildebrand et al.; U.S. Appl. No. 12/872,314 entitled "Lens Capsule Size Estimation," filed Aug. 31, 2010.

Conlisk, A. T. et al; Mass Transfer and Flow in Electrically Charged Micro- and Nano-channels; Analytical Chemistry, vol. 74; iss. 9; pp. 2139-2150; 2002.

Dubbelman et al.; The Thickness of the Aging Human Lens Obtained from Corrected Scheimpflug Images; Optometry & Vison Science; vo. 78; iss. 6; pp. 411-416; Jun. 2001.

Gorder, P. F.; Electricity can pump medicine in implanted medical devices; Ohio State Research News; 3 pgs.; May 2, 2002 (printed from internet Aug. 19, 2010).

Tehrani et al.; Capsule measuring ring to predict capsular bag diameter and follow its course after foldable intraocular lens implantation; J Cataract Refract Surg.; vol. 29; No. 11; pp. 2127-2134; Nov. 2003.

Vass et al.; Prediction of pseudophakic capsular bag diameter based on biometric variables; J Cataract Refract Surg.; vol. 25; pp. 1376-1381; 1999.

* cited by examiner

POLYMERIC MATERIALS SUITABLE FOR OPHTHALMIC DEVICES AND METHODS OF MANUFACTURE

CROSS REFERENCE TO RELATED APPLICATIONS

This application claims the benefit of U.S. Provisional Patent Application No. 60/902,593, filed on Feb. 21, 2007, the contents of which are incorporated herein by reference.

BACKGROUND OF THE INVENTION

Cataracts are a major cause of blindness in the world and the most prevalent ocular disease. Visual disability from cataracts accounts for more than 8 million physician office visits per year. When the disability from cataracts affects or alters an individual's activities of daily living, surgical lens removal with intraocular lens (IOL) implantation is the preferred method of treating the related visual limitations. In the United States, about 2.5 million cataract surgical procedures are performed annually, making it the most common surgery for Americans over the age of 65. With about 97 percent of cataract surgery patients receiving intraocular lens implants each year, the annual costs for cataract surgery and associated care in the United States is larger than $4 billion.

A cataract is defined as an opacity of a patient's lens, whether it is a localized opacity or a diffuse general loss of transparency. To be clinically significant, however, the cataract must cause a significant reduction in visual acuity or a functional impairment. A cataract occurs as a result of aging or secondary to hereditary factors, trauma, inflammation, metabolic or nutritional disorders, or radiation. Age related cataract conditions are the most common.

In treating a cataract, the surgeon removes the crystalline lens matrix from the lens capsule and replaces it with an intraocular lens ("IOL") implant. The typical IOL provides a selected focal length that allows the patient to have fairly good distance vision. After cataract surgery, however, the patient typically needs glasses for reading. This is explained by the imaging properties of the human eye, which are facilitated by several optical interfaces.

A healthy youthful human eye has a total power of approximately 59 diopters, with the anterior surface of the cornea (e.g. the exterior surface, including the tear layer) providing about 48 diopters of power, while the posterior surface provides about −4 diopters. The crystalline lens, which is situated posterior of the pupil in a transparent elastic capsule supported by the ciliary muscles, provides about 15 diopters of power, and also performs the critical function of focusing images upon the retina. This focusing ability, referred to as "accommodation," enables imaging of objects at various distances.

The power of the lens in a youthful eye can be adjusted from 15 diopters to about 29 diopters by adjusting the shape of the lens from a moderately convex shape to a highly convex shape. The mechanism generally accepted to cause this adjustment is that ciliary muscles supporting the capsule (and the lens contained therein) move between a relaxed state (corresponding to the moderately convex shape) and a contracted state (corresponding to the highly convex shape). Because the lens itself is composed of viscous, gelatinous transparent fibers, arranged in an "onion-like" layered structure, forces applied to the capsule by the ciliary muscles cause the lens to change shape.

Isolated from the eye, the relaxed capsule and lens take on a spherical shape. Within the eye, however, the capsule is connected around its circumference by approximately 70 tiny ligament fibers to the ciliary muscles, which in turn are attached to an inner surface of the eyeball. The ciliary muscles that support the lens and capsule therefore are believed to act in a sphincter-muscular mode. Accordingly, when the ciliary muscles are relaxed, the capsule and lens are pulled about the circumference to a larger diameter, thereby flattening the lens, whereas when the ciliary muscles are contracted the lens and capsule relax somewhat and assume a smaller diameter that approaches a more spherical shape.

As noted above, the youthful eye has approximately 14 diopters of accommodation. As a person ages, the lens hardens and becomes less elastic, so that by about age 45-50, accommodation is reduced to about 2 diopters. At a later age the lens may be considered to be non-accommodating, a condition known as "presbyopia". Because the imaging distance is fixed, presbyopia typically entails the need for bifocals to facilitate near and far vision.

Apart from the age-related loss of accommodation ability, such loss also has affected IOLs for the treatment of cataracts. Although the research directed at accommodating IOLs has met with some success, the relative complexity of the methods and apparatus developed to date have prevented widespread commercialization of such devices.

IOLs were made from rigid polymeric materials such as polymethyl methacrylate (PMMA), however more resilient polymeric materials are becoming increasingly more popular.

An IOL typically comprises an optic portion providing for the transmission of light, and a haptic portion extending peripherally from the optic portion.

In some IOL designs, such as those described in U.S. Pat. No. 4,932,966 to Christie et al., the optic portion of the lens comprises a thin membrane sealed along its edges to a thicker substrate to form a cavity between the two. Deformable haptics are attached to the periphery of the optic portion and are filled with a driving fluid, such a silicone oil. Movement of the ciliary muscles deforms the haptics and drives fluid from the haptics into the cavity to deflect the thin membrane of the optic portion, thereby modifying the optical power of the lens. As described in that patent, the substrate of the lens may comprise polymethyl methacrylate (PMMA), while the thin membrane and haptics may comprise a silicone elastomer.

U.S. Pat. No. 6,730,123 to Klopotek also describes a fluid-driven IOL, in which an optical fluid is transferred between an optical chamber having a flexible deformable surface and a reservoir to change the optical power of the lens. In the IOL described in that patent, the substrate, deformable surface and internal components are all formed from an acrylic elastomer.

These and other designs suffer from a number of drawbacks. For example, it is known that silicones have high permeability in silicone elastomer materials. Thus, over time, the silicones used in the above-described systems will have a tendency to diffuse through the silicone elastomers. Such diffusion results in a loss of fluid from the IOL and also effects the mechanical properties of the silicone elastomer component, thereby degrading performance of the IOL over time. In addition, silicone elastomer components are likely to permit aqueous fluids from the eye to diffuse into the IOL, further degrading performance of the IOL.

One previously known method to control diffusion of fluids into solid materials involves the deposition of a diffusion barrier on a surface of the lens. For example, U.S. Pat. No. 6,827,966 to Qiu et al. discloses diffusion-controllable coatings on ophthalmic lenses capable of controlling the out-diffusion or release of guest materials from the lenses. The coatings appear better suited for non-implantable lenses than for intraocular lenses, and are applied over the existing lens surfaces rather than being included in the polymeric composition of the lens.

A different process for permanently altering the surface properties of a lens surface, including an IOL, is the Langmuir-Blodgett deposition, described in U.S. Pat. Nos. 4,941,997, 4,973,429, and 5,068,318. Other known processes include controlled spin casting, chemisorptions, and vapor deposition.

A more recent technique developed for coating substrates is a layer-by-layer ("LbL") polymer absorption process. In particular, U.S. Pat. Nos. 5,518,767 and 5,536,573 to Rubner et al. describe methods of producing bilayers of p-type doped electrically conductive polycationic polymers and polyanions or water-soluble, non-ionic polymers on glass substrates.

U.S. Pat. No. 5,208,111 to Decher et al. describes a method for applying one or more layers to a support modified by the applications of ions and ionizable compounds of the same charges over the entire area. The one or more layers are made of organic materials, which in each layer contain ions of the same charge, the ions of the first layer having the opposite charge of the modified support and, in the case of several layers, each further layer having again the opposite charge of the previous layer.

U.S. Pat. No. 5,700,559 to Sheu et al. discloses a method for making a hydrophilic article having a substrate, an ionic polymeric layer bonded directly onto the substrate, and a disordered polyelectrolyte coating ionically bonded to the ionic polymeric layer. The ionic polymeric layer is obtained by a plasma treatment, an electron beam treatment, a corona discharge, an X-ray treatment, or an acid/base chemical modification of the substrate.

Although each of the above described surface modification techniques are effective for producing an IOL with an altered surface that is different from the remainder of the device, each of these processes requires complex and time-consuming pretreatments of the substrate surface to obtain a highly charged surface.

In addition, the above-described surface modifications involve applying coatings to the outer surfaces of the IOL, rather than providing an IOL with bulk properties that reduces diffusion of fluids into or out of the lens.

In view of the foregoing, it would be desirable to provide an ophthalmic device, such as an IOL, in which the bulk polymeric material provides enhanced resistance to diffusion of fluids into or out of the device.

In addition, it would be desirable that the polymer have properties that would allow it to be deformed to a delivery configuration to enable its implantation in the eye, yet return to a pre-implantation configuration after being implanted in the eye. In addition, it would be desirable that the polymeric composition have a sufficient high refractive index.

SUMMARY OF THE INVENTION

One aspect of the invention is a polymeric material for an ophthalmic device including butyl acrylate, trifluoroethyl methacrylate, and phenylethyl acrylate. In some embodiments the butylacrylate is present in the amount from about 35% to about 65% by volume, and in some embodiments it is present in the amount from about 45% to about 55% by volume.

In some embodiments the trifluoroethyl methacrylate is present in the amount from about 15% to about 30% by volume, and in some embodiments the trifluoroethyl methacrylate is present in the amount from about 18% to about 22% by volume.

In some embodiments the phenylethyl acrylate is present in the amount from about 20% to about 40% by volume, and in some embodiments the phenylethyl acrylate is present in the amount from about 26% to about 34% by volume.

In some embodiments the material also includes a cross-linking agent such as ethylene glycol dimethylacrylate. The material can also include an ultraviolet light absorbing material. The polymer as formed can also have a barrier coating on any surface to further enhance the polymer's resistance to the diffusion of fluid, such as, for example, silicone oil, water, or saline.

The polymeric material can be used for an intraocular lens which comprises a central optic portion and a peripheral non-optic portion. In some embodiments the central optic portion is made at least in part of the polymeric material, whereas the non-optic portion is comprised of a second polymeric material different than the polymeric material in the central optic portion. In some embodiments the central optic portion and peripheral non-optic portion are made from substantially the same polymeric material.

One aspect of the invention is a polymeric material for an ophthalmic device. The polymer includes an alkyl acrylate present in the amount from about 35% to about 65% by volume, a fluoroacrylate present in the amount from about 15% to about 30%, and a phenyl acrylate present in the amount from about 20% to about 40%. The alkyl acrylate can be butyl acrylate; the fluoroacrylate can be trifluoroethyl methacrylate; and the phenyl acrylate can be phenylethyl acrylate.

One aspect of the invention is a polymeric material for an ophthalmic device wherein the material includes an alkyl acrylate, a fluoroacrylate, and a phenyl acrylate, wherein there is an effective amount of the fluoroacrylate to provide the polymer material with a substantial resistance to the diffusion of fluid. In some embodiments the fluid is silicone oil, saline, or water. In some embodiments the substantial resistance to the diffusion of fluids comprises having a swell fraction in silicone oil that is less than about 0.02, and in some embodiments is substantially zero.

In some embodiments there is an effective amount of the alkyl acrylate to provide the polymer material with a modulus of elasticity between about 0.1 Mpa and about 0.6 Mpa. In some embodiments there is an effective amount of the phenyl acrylate to provide the polymeric composition with a refractive index between about 1.44 and about 1.52.

One aspect of the invention is a polymeric material for an ophthalmic device wherein the polymeric material has a refractive index between about 1.44 and about 1.52, a modulus of elasticity between about 0.1 Mpa and about 0.6 Mpa, and wherein the polymeric material is substantially resistant to the diffusion of fluid, such as silicone oil, water, or saline. In some embodiments the polymer is substantially resistant to the diffusion of fluid without a barrier coating layer on a surface of the polymer.

One aspect of the invention is an accommodating fluid-driven intraocular lens. The IOL includes a light-transmissive optic portion and a haptic portion extending peripherally from the optic portion. The optic portion and the haptic portion are in fluidic communication, and the haptic portion is configured so that movement of a patient's ciliary muscle causes a fluid to be displaced between the optic portion and the haptic portion. At least one of the optic portion and haptic portion comprises a polymer material comprising butyl acrylate, trifluoroethyl methacrylate, and phenylethyl acrylate. The polymeric material preferably prevents the fluid disposed within the IOL from diffusing through the polymer. In some embodiments the fluid is silicone oil.

One aspect of the invention is a method of manufacturing a polymeric material for an ophthalmic device. The method includes providing a mixed composition by adding together and mixing butyl acrylate in the amount of about 35% to about 65%, trifluoroethyl methacrylate in the amount of about 15% to about 30%, and phenylethyl acrylate in the amount of about 20% to about 40%, and then curing the mixed composition.

BRIEF DESCRIPTION OF THE DRAWINGS

The above and other objects and advantages of the present invention will be apparent upon consideration of the following detailed description, taken in conjunction with the accompanying drawings, in which like reference numerals refer to like parts throughout, and in which.

DETAILED DESCRIPTION OF THE INVENTION

The present invention relates generally to improved polymeric materials. The polymeric materials have improved resistance to the diffusion of fluid, relatively high refractive indexes, and are adapted to assume an initial configuration after being deformed during implantation in the human body. While the polymeric materials can be used in a wide variety of applications, the polymers are described herein in their use in an ophthalmic device such as an intraocular lens ("IOL"). While one use of the polymers is for a fluid-driven, accommodating IOL, the polymers can be used in a non-accommodating or non-fluid driven IOL. In addition to an IOL, the polymeric compositions of the present invention can also be used in other ophthalmic devices such as, but not limited to, contact lenses, keratoprostheses, capsular bag extension rings, corneal inlays, corneal rings, or other ophthalmic devices. An exemplary alternative use would be in the field of breast implants, such that the polymers can be used as an exterior shell-like material to prevent leakage of an internal material.

The polymeric compositions described herein may be used in an IOL, such as any of the fluid-driven IOLs described in U.S. Patent Application No. 60/433,046, filed Dec. 12, 2002, U.S. patent application Ser. No. 10/734,514, filed Dec. 12, 2003, U.S. patent application Ser. No. 10/971,598, filed Oct. 22, 2004, U.S. patent application Ser. No. 11/173,961, filed Jul. 1, 2005, U.S. patent application Ser. No. 11/252,916, filed Oct. 17, 2005, U.S. patent application Ser. No. 11/642,388, filed Dec. 19, 2006, and U.S. patent application Ser. No. 11/646,913, filed Dec. 27, 2006, the disclosures of which are hereby incorporated by reference in their entirety. The compositions may also, however, be used in a non fluid-driven IOL or a non-accommodating IOL.

A device implanted in the eye becomes exposed to the fluid in the eye. The fluid in the eye can, over time, diffuse through the device and have unintended and/or undesired effects on the physical characteristics of the device. For example, a polymeric IOL that is implanted in the eye may suffer from the diffusion of eye fluid into the IOL's polymeric material. Attempts have been made to coat ophthalmic devices with barrier layers to prevent such diffusion, but these procedures can be costly and time consuming. In addition, if an ophthalmic device contains a chamber or channel within the device which contains a fluid, there is a risk that that fluid can diffuse out of its fluid chamber and into the polymeric material. This results in a decrease in the amount of fluid that can be utilized by the IOL, as well as to possibly alter the physical characteristics of the polymeric material. Therefore, the inventive bulk polymers described herein can be used in ophthalmic devices to resist the diffusion of fluid into or out of the device.

For implantable devices that must be implanted through an incision in the sclera, it is generally desirable that the incision in the sclera be as small as possible while still being able to deform the device without damaging it. The device must also be able to reform to its initial configuration after delivery. The inventive polymers described herein can therefore be used in ophthalmic device that need to be deformed to be delivered through an incision, yet will return to their initial configuration once implanted in the eye.

Similarly, it may be desirable to increase the refractive index ("RI") of the ophthalmic device to increase its refractory power. An increase in the RI of the bulk polymer can allow the device to be thinner, yet maintain a desired power. This can also provide the device with a smaller delivery profile to reduce the size of the incision in the eye during implantation.

Improved properties of the polymers described herein include, without limitation, the modulus of elasticity, the index of refraction, the resistance to the diffusion of fluids, the responsiveness of the composition, mechanical strength, rigidity, wettability, and optical clarity. These properties are not necessarily mutually exclusive and the list is not intended to be exhaustive.

One embodiment of the invention is a polymeric material for an ophthalmic device. The polymer comprises a first component, a second component, and a third or more components. In a preferred embodiment, the composition comprises butyl acrylate, trifluoroethyl methacrylate, phenylethyl acrylate, and ethylene glycol dimethacrylate as a cross-linker. These monomers are not intended to be limiting and are provided by way of example.

To achieve the desired properties of the polymer described above, it is contemplated that particular monomers or other components may be selected to achieve specific properties, or that particular monomers and other components may be selected in combination to achieve specific properties.

Butyl acrylate, for example, a rubbery material, generally enhances the responsiveness of the polymeric material. Alternatives for butyl acrylate include alkyl acrylates and other monomers with suitable responsiveness properties. Alternatives for butyl acrylate which may demonstrate responsive properties include, without limitation, octyl acrylate, dodecyl methacrylate, n-hexyl acrylate, n-octyl methacrylate, n-butyl methacrylate, n-hexyl methacrylate, n-octyl methacrylate, 2-ethylhexyl acrylate, 2-ethylhexyl methacrylate, 2,2-dimethylpropyl acrylate, 2,2-dimethylpropyl methacrylate, trimethylcyclohexyl acrylate, trimethylcyclohexyl methacrylate, isobutyl acrylate, isobutyl methacrylate, isopentyl acrylate, isopentyl methacrylate, and mixtures thereof. In addition, alternatives for butyl acrylate may include a branched chain alkyl ester, e.g. 2-ethylhexyl acrylate, 2-ethylhexyl methacrylate, 2,2-dimethylpropyl acrylate, 2,2-dimethylpropyl methacrylate, trimethylcyclohexyl acrylate, trimethylcyclohexyl methacrylate, isobutyl acrylate, isobutyl methacrylate, isopentyl acrylate, isopentyl methacrylate and mixtures thereof.

In some embodiments butyle acrylate is present in the range from about 10% to about 80% by volume, and in some embodiments is present in the range from about 20% to about 70% by volume. In preferred embodiments butyl acrylate is present in the range from about 35% to about 65% by volume, and in more preferred embodiments from about 45% to about 65% by volume. All percentages recited herein are considered to be "by volume," unless specifically stated otherwise.

In some embodiments the polymer has a modulus of elasticity ranging from about 0.1 to about 0.6 Mpa. In some embodiments the modulus is between about 0.1 to about 0.3 Mpa.

Trifluoroethyl methacrylate, or suitable alternatives, can be added to the polymeric material to enhance the polymer's resistance to the diffusion of fluids as described herein. Generally, using a monomer with more fluorine atoms will enhance the polymer's resistance to the diffusion of fluid.

While the ethyl group of trifluoroethyl can potentially bind up to 5 fluorine atoms, a large number of fluorine atoms can reduce the refractive index of the polymer. In some embodiments, therefore, trifluoroethyl methacrylate will provide a desired balance between the polymer's resistance to diffusion and the polymer's refractive index.

Fluorocarbon monomers can enhance the polymer's resistance to the diffusion of fluid and some can be used as substitutes for trifluoroethyl methacrylate. Alternatives for trifluoroethyl methacrylate include fluoroacrylates and other monomers with that provide that polymer with suitable resistance to diffusion properties. Alternatives for trifluoroethyl methacrylate include, without limitation, heptadecafluorodecyl acrylate, heptadecafluorodecyl methacrylate, hexafluorobutyl acrylate, hexafluorobutyl methacrylate, tetrafluoropropyl methacrylate, octafluoropentyl acrylate, octafluoropentyl methacrylate, dodecafluoroheptyl methacrylate, heptafluorobutyl acrylate, trifluoroethyl acrylate, hexafluoro-iso-propyl methacrylate, pentafluorophenyl acrylate, and pentafluorophenyl methacrylate.

In some embodiments trifluoroethyl methacrylate is present in the range from about 5% to about 70%, and in some embodiments it is present in the range from about 10% to about 50%. In preferred embodiments it is present in the range of about 15% to about 30%, and in more preferred embodiments it is present in the range of about 18% to about 22%.

Phenylethyl acrylate, or suitable alternatives, can be included in the polymeric composition to increase the refractive index of the polymer. Phenyl groups in general can increase the refractive index of the polymer. Alternatives for Phenylethyl acrylate include phenyl acrylates and other monomers with that provide that polymer with suitably high refractive index.

Other groups which can be used to increase the refractive index of the polymer include, without limitation, benzyl (benzoyl), carbazole-9-yl, tribromophenyl, chlorophenyl, and pentabromophenyl. Exemplary monomers that can be used as alternatives to phenylethyl acrylate include, without limitation, tribromophenyl acrylate, 2-(9H-Carazole-9-yl)ethyl methacrylate, 3-chlorostyrene, 4-chlorophenyl acrylate, benzyl acrylate, benzyl methacrylate, benzyl methacrylamide, n-vinyl-2-pyrrolidone, n-vinylcarbazole, pentabromophenyl acrylate, and pentabromophenyl methacrylate, phenylethyl methacrylate, 2-phenylpropyl acrylate, or 2-phenylpropyl methacrylate.

In some embodiments phenylethyl acrylate is present in the range from about 5% to about 60%, while in some embodiments it is present in the range of about 10% to about 50%. In preferred embodiments it is present in the range of about 20% to about 40%, and in more preferred embodiments it is present in the range of about 26% to about 34%.

In some embodiments the polymer has a refractive index of between about 1.44 to about 1.52. In some embodiments the refractive index is between about 1.47 and about 1.52. In some embodiments the refractive index is between about 1.47 and about 1.5.

In some embodiments the composition also includes a cross-linking agent, such as ethylene glycol dimethacrylate. Examples of suitable crosslinking agents include but are not limited to diacrylates and dimethacrylates of triethylene glycol, butylene glycol, neopentyl glycol, ethylene glycol, hexane-1,6-diol and thio-diethylene glycol, trimethylolpropane triacrylate, N,N'-dihydroxyethylene bisacrylamide, diallyl phthalate, triallyl cyanurate, divinylbenzene; ethylene glycol divinyl ether, N,N'-methylene-bis-(meth)acrylamide, sulfonated divinylbenzene, divinylsulfone, ethylene glycol diacrylate, 1,3-butanediol dimethacrylate, 1,6 hexanediol diacrylate, tetraethylene glycol dimethacrylate, trifunctional acrylates, trifunctional methacrylates, tetrafunctional acrylates, tetrafunctional methacrylates and mixtures thereof.

Cross-linking agents may be present in amounts less than about 10%, less than about 5%, less than about 2%, or less than about 1%. The cross-linking agent(s) can cause the polymers to become interlaced within a tri-dimensional space, providing for a compact molecular structure having an improved elastic memory, or responsiveness, over the non-crosslinked composition.

In some embodiments of the invention the polymeric compositions also includes one or more ultraviolet (UV) light absorbing materials, such as an acrylate or methacrylate functionalized benzotriazole or benzophenone, in amounts less about 5%. In some embodiments the UV light absorbing material(s) is present in the range from about 0.05% to about 2%. Suitable ultraviolet light absorbers for use in the present invention include, without limitation, β-(4-benzotriazoyl-3-hydroxyphenoxy)ethyl acrylate, 4-(2-acryloyloxyethoxy)-2-hydroxybenzophenone, 4-methacryloyloxy-2-hydroxybenzophenone, 2-(2'-methacryloyloxy-5'-methylphenyl) benzotriazole, 2-(2'-hydroxy-5'-methacryloyloxyethylphenyl)-2H-benzotriazole, 2-[3'-tert-butyl-2'-hydroxy-5'-(3"-methacryloyloxypropyl)phenyl]-5-chloro-benzotriazole, 2-[3'-tert-butyl-5'-(3"-dimethylvinylsilylpropoxy)-2'-hydroxyphenyl]-5-m-ethoxybenzotriazole, 2-(3'-allyl-2'-hydroxy-5'-methylphenyl)benzotriazole, 2-[3'-tert-butyl-2'-hydroxy-5-(3"-methacryloyloxypropoxy)phenyl]-5-chloro-benzotriazole and 2-[3'-tert-butyl-2'-hydroxy-5'-(3"-methacyloyloxypropoxy)phenyl]-5-chloro-benzotriazole. One skilled in the art will appreciate that different other chemistries of UV light absorbants may be selected.

One or more suitable free radical thermal polymerization initiators may be added to the polymeric compositions described herein. Examples of such initiators include but are not limited to organic peroxides, such as acetyl peroxide, lauroyl peroxide, decanoyl peroxide, stearoyl peroxide, benzoyl peroxide tert-butyl peroxypivalate, peroxydicarbonate, and the like. Such an initiator can be added in the range of about 0.01% to about 1% of the total polymer mixture.

Alternative UV initiators include those known in the field such as, for example but not limited to, benzoin methyl ether, benzoin ethyl ether, Darocur® 1173, 1164, 2273, 1116, 2959, 3331 (EM Industries) and Irgacur® 651 and 184 (Ciba-Geigy, Basel, Switzerland).

The diffusion resistant properties of the inventive polymers described herein may be further enhanced by providing a barrier layer on the exterior surface of the ophthalmic device. In addition, if the device comprises a fluid chamber disposed within the device (such as a fluid chamber disposed in a fluid-driven accommodating IOL), the device can also have a barrier layer on the inner surface of the fluid chamber to increase the resistance to diffusing out of the fluid chamber. The barrier layer can be a thin layer of a fluorocarbon materials or polymers, examples of which include hexafluoroethane, hexafluoropropylene, hexafluoropropane, octofluoropropane, polytetrafluoroethylene, and 1H, 1H, 2H-perfluoro-1-dodecene. The barrier layer can be deposited or covalently bonded on the solid surfaces of the ophthalmic device, either individually or in combination through a variety of manufacturing processes. One common manufacturing process is plasma deposition.

The layers formed by plasma deposition will generally be very thin, for example, from about 20 to about 100 nanometers. Because fluorocarbon polymers generally have low refraction indices, a barrier layer with a thickness that is less than a quarter of the wavelength of visible light will not be seen with the naked eye.

As stated above, the inventive polymers described herein may be used in an IOL with fluid disposed therein, such as in fluid chambers. In general, the viscosity of a fluid is related to the diffusion properties of the fluid; a low viscosity fluid can more easily diffuse through the polymer.

An ophthalmic device may contain silicone oil. The amount of silicone oil that diffuses through the polymer can be reduced by selecting a silicone oil with narrow molecular weight distribution, in particular with the removal of low molecular weight silicone oil molecules. A sequence of stripping processes is commonly used to remove low molecular weight components in silicone oil. In general, low molecular weight components will diffuse faster than higher molecular components. However, higher molecular weight components contribute to an increase in the viscosity which requires a greater force to drive the fluid throughout the IOL. Therefore, silicone oil with a narrow molecular weight distribution is preferred. The fluid disposed within the ophthalmic device is not limited to silicone oil and can be, for example, a saline solution.

In some embodiments, however, the IOL components are substantially index matched, such that the deflection of one of the surfaces of the IOL contributes significantly to any change in power during accommodation. For example, the bulk polymer will be substantially indexed matched to any fluid within the IOL. Substantially index-matched, as that phrase is used herein, include minimal differences in refractive indexes between components of the IOL. For example, if adhesives are used in the manufacturing of an IOL, those adhesives may have different refractive indexes but those differences will be negligible when considering the overall power changes of the accommodating IOL.

In some embodiments the $T_G$ of the polymer is about $-20°$ C., and can stretch to about 4× the length without breaking.

Figure 1A:
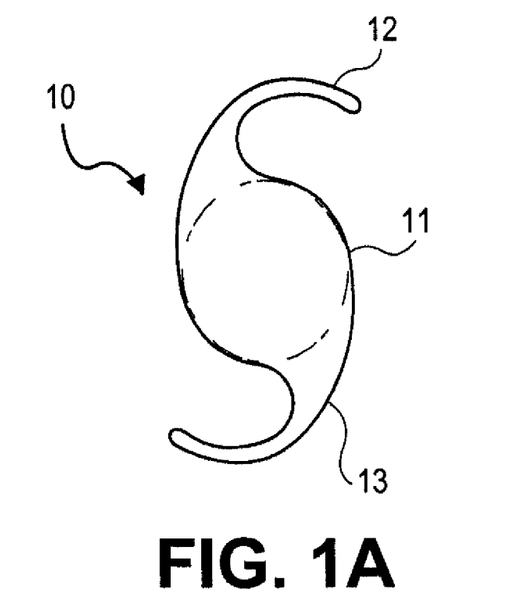
FIGS. 1A-1C illustrate exemplary non-fluid driven intraocular lenses, at least part of which may comprise the polymeric materials of the present invention.
Figure 1B:
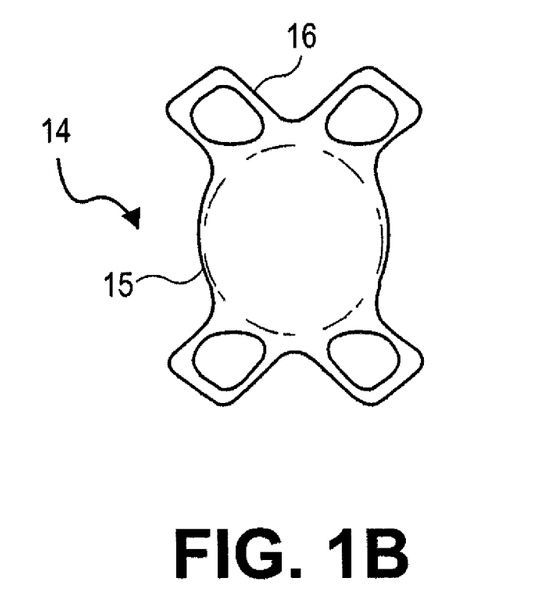
Figure 1C:
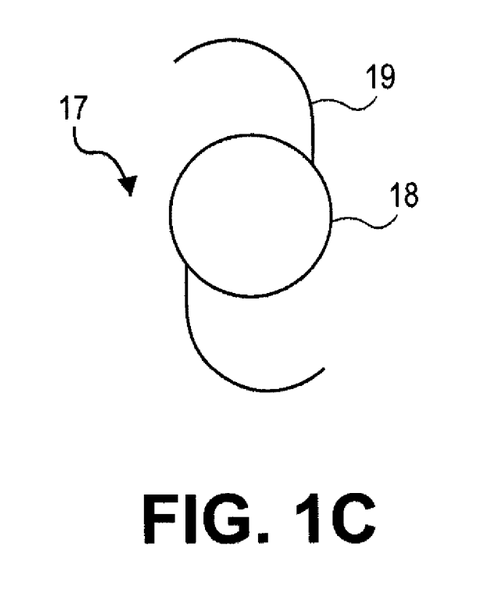

FIGS. 1A-1C illustrate exemplary static IOLs in which the polymeric materials described herein may be used. Intraocular lenses 10, 14 and 17 typically comprise an optic portion (11, 15, and 18, respectively) providing for the transmission of light, and a haptic portion (12, 16, and 19, respectively) extending peripherally from the optic portion and adapted to engage the capsular bag.

The optics portion and the haptic portion(s) may be comprised of the same polymeric composition or may be comprised of different compositions. The composition of the optics and haptic(s) portions may depend on which properties are desired in each of the components. For example, it may not be necessary to achieve a high refractive index in the haptics portion as the haptics do not generally contribute to the focusing of light, and thus a polymer used for the haptics may not need a high refractive index. Similarly, for example, it may be desirable for the haptics portion to possess different responsiveness properties than the static optics portion.

Figure 2:
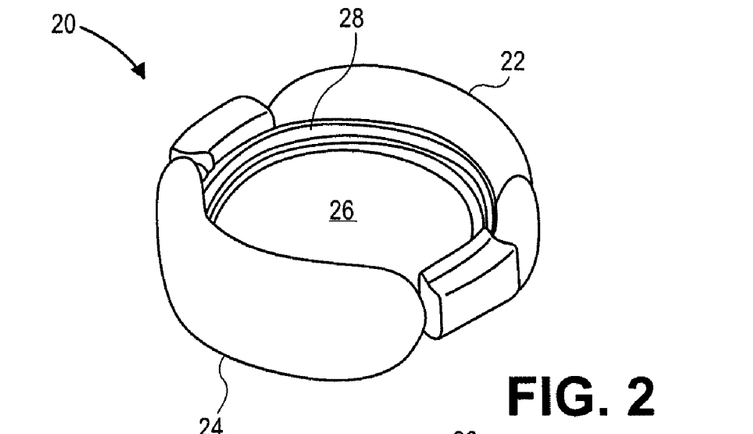
FIGS. 2-4 illustrate an exemplary fluid-driven IOL, at least part of which may comprise the polymeric materials of the present invention.
Figure 3:
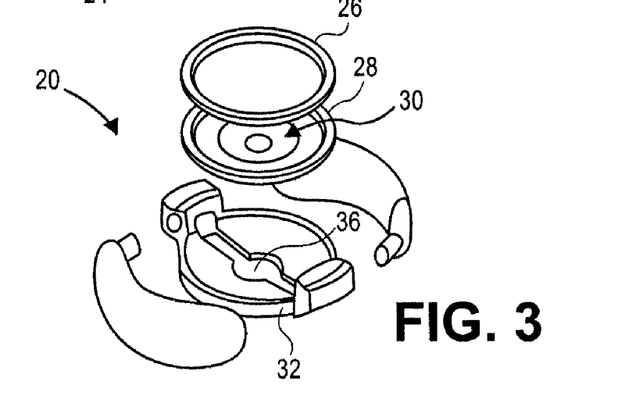
Figure 4:
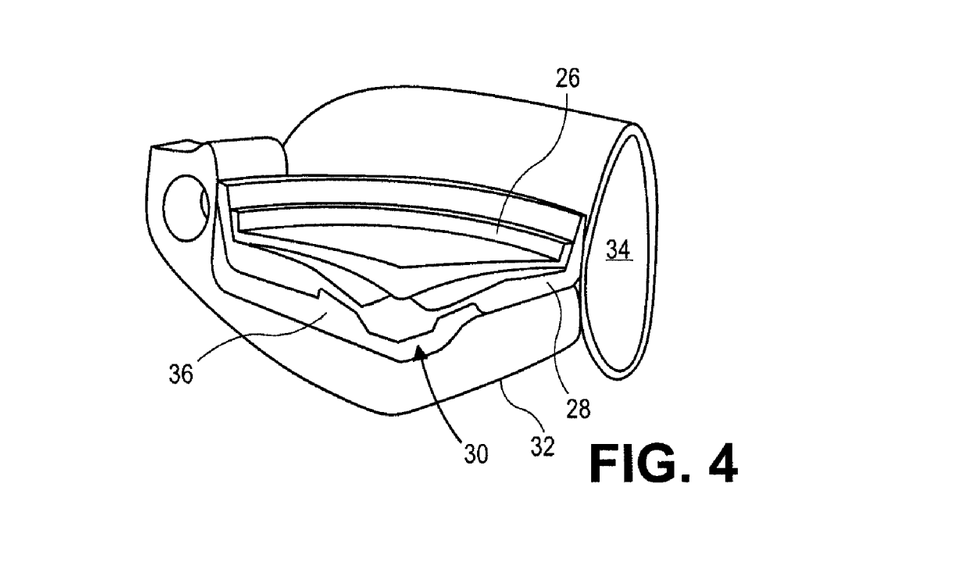

FIGS. 2-4 illustrate an exemplary embodiment of an accommodating IOL, at least part of which (e.g., the central optic portion) may comprise a polymeric composition of the present invention. IOL 20 includes haptics 22 and 24, anterior lens element 26, intermediate layer 28 which comprises actuator 30, and substrate 32. Haptics 22 and 24 define interior volumes 34 which are in fluid communication with channel and well 36 formed between substrate 32 and intermediate layer 28. As shown, actuator 30 is integral with intermediate layer 28. Actuator 30 is in fluid communication with deformable haptics 22 and 24 which distribute a fluid between the interior volume of the haptics and channel and well 36. Deformation of the haptics resulting from movement of the ciliary muscles forces fluid in the haptics into channel and well 36. The fluid in the well applies a force to actuator 30, which transmits the force to anterior lens element to distend the anterior lens element in the anterior direction, thus increasing the optical power of the lens.

A number of experiments were carried out to achieve compositions with desired properties. In a first experiment, butyl acrylate (BuA) was tested as an alternative to PMMA for use in the non-fluidic portions of the IOL (i.e., the bulk polymer). BuA is more flexible than PMMA and, like all acrylic polymers, also has a high level of atacticity which provides for low crystallinity, adequate processing characteristics, high optical quality, and long term stability to ultraviolet (UV) light. Tests indicated that solid lens components manufactured from BuA exhibited improved responsiveness to movements of the ciliary muscles in comparison to the same components manufactured from PMMA, but at the same time no marked increase could be observed over the PMMA components in terms of resistance to diffusion of IOL and eye fluids.

In a second experiment, solid lens components were produced comprising a copolymer of BuA and trifluoroethyl methacrylate (TFEMA). This composition was compared with components manufactured from BuA alone. Adding TFEMA in from about 20% to about 30% caused the lens components to retain the same desirable responsiveness to movements of the ciliary muscles as the unmodified BuA components, and also resulted in a marked improvement in diffusion resistance to IOL fluids and eye fluids (which can be observed by, for example, measuring the swell fraction described below). However, this composition exhibited a decrease in the refractive index. Such BuA-TFEMA compositions as described above may be suitable for use in IOL components that do not require optical clarity, for example, in the haptic portion of an IOL. Such compositions also have utility in non-ophthalmologic applications, such as for use in breast implants, where a responsive material highly resistant to fluid diffusion is desirable.

In a third experiment, phenylethyl acrylate (PhEA) was copolymerized together with the BuA-TFEMa composition from above. A sharp increase in the refractive index of this composition was observed, particularly when BuA was present from about 30% to about 60%, when PhEA was present from about 20% to about 40%, and when TFEMA was present from about 20% to about 50%. More specifically, an increase of the refractive index to 1.477 was obtained, with an elastic modulus measured in the 0.1-0.3 Mpa range. Importantly, IOL solid components manufactured from this composition proved to have an excellent resistance to diffusion and a high responsiveness to movements of the ciliary muscles.

In a fourth experiment, a cross-linking agent was added to the BuA-PhEA-TFEMA composition as an additional constituent. In particular, ethylene glycol dimethacrylate was found to operate as a suitable cross-linking agent with this composition. The foregoing cross-linking agents may be added in amounts of less than about 5% of the BuA-TFEMA-PhEA composition and cause the composition polymers to become interlaced within a tri-dimensional space, providing for a compact molecular structure having an improved elastic memory over the non-crosslinked composition. The resulting compositions also showed improved diffusion resistance.

When IOL solid components were manufactured from BuA-TFEMA-PhEA-EGDMA compositions, and included an optional barrier layer, improvements in diffusion resistance of the IOL were observed that were up to 40 times greater than the material without the barrier coating. Additionally, these solid components were biocompatible, optically clear, had a high refractive index and desirable levels of mechanical strength. These components also exhibited a level of flexibility and elastic memory sufficient to permit the IOL to be inserted without breaking through a small incision in the cornea, and later capable of regaining its original shape within an acceptable amount of time.

To test a polymer's resistance to diffusion, a swell study can be performed which detects how much a polymeric sample with known dimensions and weight swells when in contact with a fluid. The test measures solubility but not necessarily diffusivity and can be accomplished as follows:

Prepare a sample polymer of known dimensions and weight (e.g., 1 cm×2 cm); add fluid (e.g. silicone oil); heat to a desired temperature (e.g., 35-37 C); at various time points, measure the sample's dimensions and weight and compare these to the original dimensions and weight. This tests how much the sample's dimensions and weight increased, or rather, how much the polymer "swelled".

A diffusion study can also be performed which measures diffusivity rather than solubility, both of which are preferably small in the compositions described herein. The test can be performed as follows:

Prepare a thin film of the sample polymer (about 100 microns thick and 25 mm in diameter); mount the film between two reservoirs of fluid—one reservoir is the driving fluid such as silicone oil, and the other fluid is a saline solution; next, sample the saline reservoir over time to determine the content of the silicone oil that has diffused through the thin film polymer to measure diffusion of the silicone oil.

The following non-limiting examples illustrate certain aspects of the present invention.

EXAMPLE 1

The following formulation is added together and mixed well:

|  | Quantity | % Quantity |
| --- | --- | --- |
| Trifluoroethyl methacrylate | 4 ml | 19.6% |
| Butyl acrylate | 10 ml | 49.0% |
| Phenyl ethyl acrylate | 6 ml | 29.4% |
| Ethylene glycol dimethacrylate | .2 ml | .980% |
| Darocur 1173 (UV initiator) | .2 ml | .980% |

Pour the formulation into a two-part mold cavity made of polypropylene, polymethylpentene, or glass. Seal the mold with no air entrapment.

Polymer curing is carried out by placing the sealed mold inside a chamber equipped with UV lamps such as Sankyo Denki Black Light Blue Lamp. Polymerization can be carried out in one hour or less depending on the lamp intensity. Optional postcuring can be carried out in thermal oven at 90 C to 100 C for 1-2 hours to ensure more complete polymerization.

The resulting polymer has a swell fraction of 0 in silicone oil, a refractive index of 1.477, and a modulus of elasticity of 0.163 Mpa.

EXAMPLE 2

The following formulation is add together, mixed well, and processed the same the formulation in Example 1:

|  | Quantity | % Quantity |
| --- | --- | --- |
| Trifluoroethyl methacrylate | 4 ml | 19.5% |
| Butyl acrylate | 12 ml | 58.5% |
| Phenyl ethyl acrylate | 4 ml | 19.5% |
| Ethylene glycol dimethacrylate | .3 ml | 1.46% |
| Darocur 1173 (UV initiator) | .2 ml | .976% |

The resulting polymer has a swell fraction of 0.019, a refractive index of 1.473, and a modulus of elasticity of 0.27 Mpa.

While illustrative embodiments of the invention are described above, it will be apparent to one skilled in the art that various changes and modifications may be made therein without departing from the invention.

What is claimed is:

1. A polymeric material for an ophthalmic device, the polymeric material comprising:
   butyl acrylate, trifluoroethyl methacrylate, and phenylethyl acrylate.

2. The material of claim 1 wherein the butylacrylate is present in the amount from about 35% to about 65% by volume.

3. The material of claim 2 wherein the butylacrylate is present in the amount from about 45% to about 55% by volume.

4. The material of claim 1 wherein the trifluoroethyl methacrylate is present in the amount from about 15% to about 30% by volume.

5. The material of claim 4 wherein the trifluoroethyl methacrylate is present in the amount from about 18% to about 22% by volume.

6. The material of claim 1 wherein the phenylethyl acrylate is present in the amount from about 20% to about 40% by volume.

7. The material of claim 1 wherein the phenylethyl acrylate is present in the amount from about 26% to about 34% by volume.

8. The material of claim 1 wherein the butylacrylate is present in the amount from about 35% to about 65% by volume, the trifluoroethyl methacrylate is present in the amount from about 15% to about 30% by volume, and the phenylethyl acrylate is present in the amount from about 20% to about 40% by volume.

9. The material of claim 8 wherein the butylacrylate is present in the amount from about 45% to about 55% by volume, the trifluoroethyl methacrylate is present in the amount from about 18% to about 22% by volume, and the phenylethyl acrylate is present in the amount from about 26% to about 34% by volume.

10. The material of claim 1 further comprising a cross-linking agent.

11. The material of claim 10 wherein the cross-linking agent is ethylene glycol dimethylacrylate.

12. The material of claim 1 further comprising an ultraviolet light absorbing material.

13. The material of claim 1 wherein the ophthalmic lens is an intraocular lens, wherein the intraocular lens comprises an central optic portion and a peripheral non-optic portion, and wherein the central optic portion is comprised of the polymer material, and wherein the non-optic portion is comprised of a second polymer material different than the polymer material.

14. A method of manufacturing the polymeric material for the ophthalmic device of claim 1, comprising: providing a mixed composition by adding together and mixing butyl acrylate in the amount of about 35% to about 65% by volume, trifluoroethyl methacrylate in the amount of about 15% to about 30% by volume, and phenylethyl acrylate in the amount of about 20% to about 40% by volume; and curing the mixed composition.

* * * * *